United States Patent [19]

Best

[11] Patent Number: 5,317,760
[45] Date of Patent: Jun. 7, 1994

[54] SEAL INDICATOR SURGICAL GLOVE OR BODY COVERING

[76] Inventor: Paul S. Best, 408 Whitney Ave., New Haven, Conn. 06511

[21] Appl. No.: 890,220

[22] Filed: May 29, 1992

[51] Int. Cl.⁵ .................... A41D 13/10; A61F 6/04
[52] U.S. Cl. .................................... 2/161.7; 2/167; 128/844; 428/69; 428/916
[58] Field of Search .................. 2/2.5, 21, 161 R, 167, 2/168, 169, 16; 604/349, 353; 128/842, 844; 428/69, 71, 916; 116/266, 270, 70; 206/524.8

[56] References Cited

U.S. PATENT DOCUMENTS

| | | | |
|---|---|---|---|
| 3,173,150 | 3/1965 | Mohler | 2/167 |
| 3,633,216 | 1/1972 | Schonholtz | 2/168 |
| 4,295,566 | 10/1981 | Vincek | 428/916 X |
| 4,742,578 | 5/1988 | Seid | 2/16 |
| 4,843,014 | 6/1989 | Cukier | 2/168 |
| 4,847,918 | 7/1989 | Sturm | 2/167 |
| 4,877,143 | 10/1989 | Travisano | 116/270 |
| 4,901,372 | 2/1990 | Pierce | 2/167 |
| 4,919,966 | 4/1990 | Shlenker | 427/2 |
| 4,930,522 | 6/1990 | Busnel et al. | 604/349 |
| 4,961,734 | 10/1990 | Kassman | 604/349 |
| 5,045,341 | 9/1991 | Shlenker | 2/167 |
| 5,133,087 | 7/1992 | Machida et al. | 2/168 |

Primary Examiner—Clifford D. Crowder
Assistant Examiner—Amy B. Vanatta
Attorney, Agent, or Firm—Robert A. Seemann

[57] ABSTRACT

Two layers of flexible material, each of which is resistant to the passage of fluids and microbes, include spacers between them, and are hermetically sealed, for maintaining reduced atmospheric pressure in the space between them. Open cell foam supported in the space is compressed by the layers until one of the layers is torn, upon which the resulting increase in atmospheric pressure in the space allows the foam to resile, increasing the space between the layers as a warning to the user of the break. An electric switch which is responsive to pressure change is in communication with the space to also signal a warning of the break.

16 Claims, 4 Drawing Sheets

SEAL INDICATOR SURGICAL GLOVE OR BODY COVERING

BACKGROUND OF THE INVENTION

1. Field of the Invention

This invention relates in general to a surgical glove, or similar protective apparel which provides a septic barrier between the user and the application, and more particularly in which the protective apparel is designed to respond to and indicate diminution in the effectiveness of the barrier.

2. Description of the Prior Art

The art is replete with gloves and similar body coverings which can provide a septic barrier between the user and the application.

U.S. Pat. No. 3,173,150, patented by R. E. Mohler on Mar. 16, 1965, discloses a glove of a laminated construction comprising open celled foam insulating material between inner and outer fabric layers to which it is in bonded connection throughout the glove to form a unitary structure. The inner layer forms a glove lining. At least the palm portion of the glove has an elastomeric water-repellant coating infused in the outer fabric layer. In order to prevent impregnation of the foam by the water-repellant elastomeric coating, the cells at the surface of the foam are collapsed.

U.S. Pat. No. 3,633,216, patented Jan. 11, 1972 by George J. Schonholtz, describes a rubber surgical glove having a finger stall constructed of an inner and an outer layer which are spaced from one another. The space between the layers is filled with any conventional indicator substance such as colored saline solution. If the cover is ruptured or pierced, the indicator will leak out through the resistant opening and contrasting color the exterior of the cover, so that a surgeon will immediately be made aware of the rupture. The indicator substance may also include a conventional antibacterial substance such as hexachlorophane.

U.S. Pat. No. 4,901,372, patented Feb. 20, 1990 by William S. Pierce, describes a surgical glove of tri-laminar construction comprising a continuous inner barrier layer, a continuous outer barrier layer, and a continuous central layer of flexible, resilient and puncture-resistant closed cell foam between the inner and outer layers. The inner and outer layers are formed of flexible, resilient, and imperforate material.

Each of the three layers help to resist needle puncture. Preferably the foam central layer is made of closed cells so that the layer forms a closed third barrier against contamination. The foam barrier closes a needle puncture path and resists subsequent contamination along the puncture path. The tri-laminar construction has an advantage over a two-layer construction in that the foam prevents spread of viral or bacterial contamination that would otherwise occur along a joined interface between two layers when a layer is punctured.

U.S. Pat. No. 4,919,966, patented by Robin R. T. Shienker on Apr. 24, 1990 discloses a covering such as a glove, condom, or sheath for the extremity of a person, comprising two layers, each layer being an array of side by side, sealed chambers, with each chamber containing a sterilizing fluid. The layers are arranged so that the chambers of one layer bridge the spaces between the chambers of the other layer, so that it is likely that accidental puncture of the covering by a needle or scalpel will open a chamber, releasing the sterilizing fluid to protect the user and application from cross infection by microbes.

In another embodiment of the '966 invention, the covering comprises a sponge-like layer of material comprising a plurality of chambers containing the sterilizing fluid. The chambers are in sufficient quantity so that accidental puncture of the covering by needle, scalpel or the like will have a high likelihood of puncturing at least one of the chambers and release the sterilizing fluid.

SUMMARY OF THE INVENTION

It is one object of the present invention to provide a septic barrier covering which resists microbial contamination between the user of the covering and the application for the barrier.

It is another object to provide additional protection against contamination by including a space at reduced atmospheric pressure within the covering, for drawing a contaminated liquid away from a puncture through the covering before it can pass completely through the covering by way of the puncture.

It is another object to provide in the septic barrier covering, means for warning the user when a surface layer of the barrier is punctured, cut or otherwise broken.

It is an object of the invention that the above means for warning responds to an increase in the reduced atmospheric pressure, thus warning of a break in a surface layer of the barrier.

Another object is that the means for warning provides an audible warning.

Another object is that the covering includes folds which include a colored area which forms a color-contrasting indication of an increase in the reduced atmospheric pressure.

Still another object of the invention is to provide a surgical glove with the above objects and advantages.

Yet another object of the invention is to provide a septic barrier covering with the above objects and advantages which directs contamination entering through a break through the covering, away from passage completely through the covering. Additional objects and advantages of the present invention will become apparent upon reading the ensuing description of the invention.

The invention provides a septic barrier covering which includes first and second layers, each being flexible and resistant to the passage of fluids such as water and air, and microbes.

Spacing means is supported between the layers.

The spacing means separates the layers, establishing or forming a space resulting from the spacing means between them for containing a reduced atmospheric pressure, and the layers are hermetically sealed with one another for maintaining the reduced atmospheric pressure in the space between them. The space is at a reduced atmospheric pressure. Means for indicating an increase in the atmospheric pressure between the layers is in communication with the space between them for sensing the pressure.

The spacing means may be compressible so that the spacing means will compress to yield a smaller spacing when it is squeezed by the first and second walls, and the spacing means further may be resilient so that it will resile when the squeezing force from the first and second layers is reduced.

Folds on the barrier covering, which part when the atmospheric pressure between the first and second layers increases, indicate that a leak of environmental atmospheric pressure through one of the layers into the space between the layers has occurred.

Other indicators of increase in atmospheric pressure between the layers include resilient means for displacing a portion of one of the first and second layers in response to the increase, a hollow expandable patch on the first layer outside the space between the layers, electrical switch means responsive to pressure change, connected to the barrier covering for sensing the atmospheric pressure between the layers, and means for generating an audible signal that is integrally attached to the barrier covering and connected to the switch means.

In one embodiment of the invention, the septic barrier covering is formed in the shape of a surgical glove. One of the above indicating means as desired, is included in the glove to indicate a break in one of the layers of the septic barrier covering.

In another embodiment of the invention, the septic barrier covering is formed in the shape of a condom. Preferably, the condom incorporates the audible signal indicator.

BRIEF DESCRIPTION OF THE DRAWINGS

In order that the invention be more fully comprehended, it will now be described, by way of example, with reference to the accompanying drawings, in which.

DESCRIPTION OF THE PREFERRED EMBODIMENTS

Before explaining the invention in detail, it is to be understood that the invention is not limited in its application to the detail of construction and arrangement of parts illustrated in the drawings since the invention is capable of other embodiments and of being practiced or carried out in various ways. It is also to be understood that the phraseology or terminology employed is for the purpose of description only and not of limitation.

Figure 1:
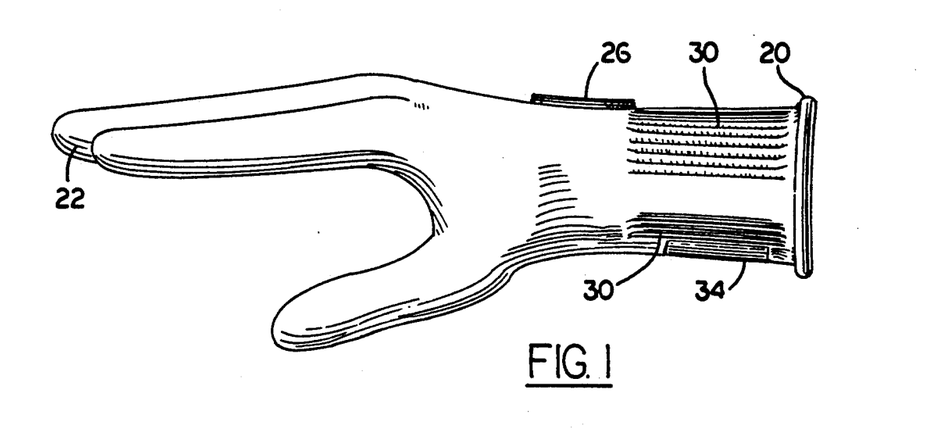
FIG. 1 is a perspective view of a surgical glove according to the present invention having four means for warning of puncture.

Referring to FIG. 1, four features on surgical glove 20 provide warning of puncture or break in the outer surface of the glove, indicating diminution in the effectiveness of the septic barrier provided by the glove.

Expandable patch 26 rises, folds 30 spread apart, audible chirp alarm 34 sounds, and the glove covering thickens, when the outer surface of the glove is punctured.

Figure 2:
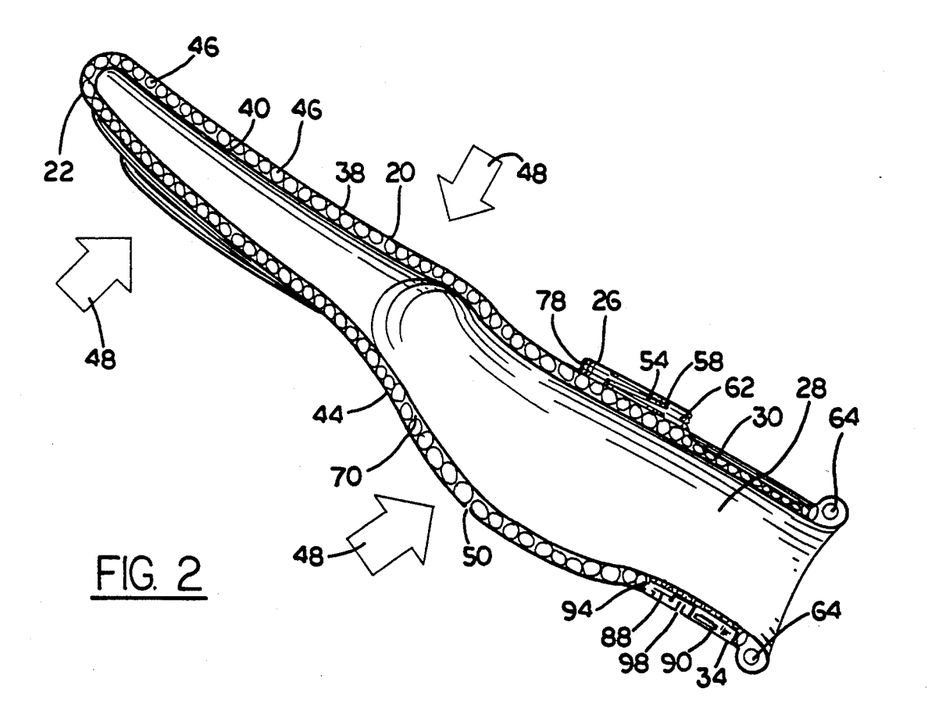
FIG. 2 is a cross section view through the index finger of the glove shown in FIG. 1.

In FIG. 2, latex outer layer 38 and inner layer 40 of covering 44 of glove 20 are impervious to passage through them of liquid, air and microbes, in the manner of surgical glove material.

Shown in cross section through the index finger 22, mid-hand 24, and wrist region 28, layers 38 and 40 are spaced from one another by flexible, resilient nodule spacers 46 attached to layer 38.

When layers 38 and 40 are unbroken and hermetic seals 64 are intact, innerspace 70 caused by spacers 46 is maintained at a reduced atmospheric pressure.

The term herein "reduced atmospheric pressure" means any pressure that is lower than that of the surrounding environment, and includes a vacuum. A near vacuum is preferred for manufacturing convenience.

The difference between greater environmental atmospheric pressure 48 upon layers 38 and 40, and lesser atmospheric pressure in space 70, causes layers 38 and 40 to squeeze resilient nodule spacers 46 between them, resulting in a thin covering 44.

When outer layer 38 or inner layer 40 is broken as at 50, or the hermetic seal between them is broken, the atmospheric pressure within space 70 equalizes with the environmental pressure which enters space 70 through the break. Squeezing force by the layers upon the spacers is reduced, and the spacers resile to increase the spacing between the layers.

Consequently, a user of glove 20 will be aware of the apparent change in thickness of covering 44 and tactile experience of the glove, and be warned of the reduced effectiveness of the septic barrier.

Further indication to the user of break in one of the two layers is provided by expandable patch 26 which contains a compressible, resilient material such as foam, or a coil spring 54. Opening 60 provides an air pressure communication passageway between inner space 62 of expandable patch 26, and inner space 70 caused by spacers 47 separating outer and inner layers 38 and 40.

When space 70 is at reduced atmospheric pressure, patch 26 is collapsed against layer 38, as spring 54 is compressed by pressure plate 58 reacting to the greater environmental pressure.

When space 70 is at environmental pressure caused by a break in the hermetic seal, patch 26 raises under the unbalanced force of spring 54, revealing to the user the raised patch with colored bands 78, that were formerly less visible in the collapsed folds of patch 62.

Still further indication to the user of break in one of the two layers is provided by axial creases or folds 30 in outer layer 38, at the wrist area of the glove when the user is wearing the glove. When the space between outer layer 38 and inner layer 40 increases upon equalization between space 70 atmospheric pressure and environmental pressure 48, the diameter of outer layer 38 increases at the wrist area, spreading folds 30 and revealing color within the folds which was formerly less visible in the collapsed folds. The spread folds and the color provide visual warning of the break.

Still further indication to the user of break in one of the two layers is provided by audible chip alarm which includes atmospheric sensitive pressure switch 88 connected to audible signal chip and battery circuit 90 for providing an audible alarm such as a chirping or beeping sounds.

Switch 88 senses atmospheric pressure in space 70 via opening 94, for detecting increase in the pressure in space 70. Optional opening 98 is provided when it is desired to have the switch responsive to a comparison with environmental atmospheric pressure.

Figure 3:
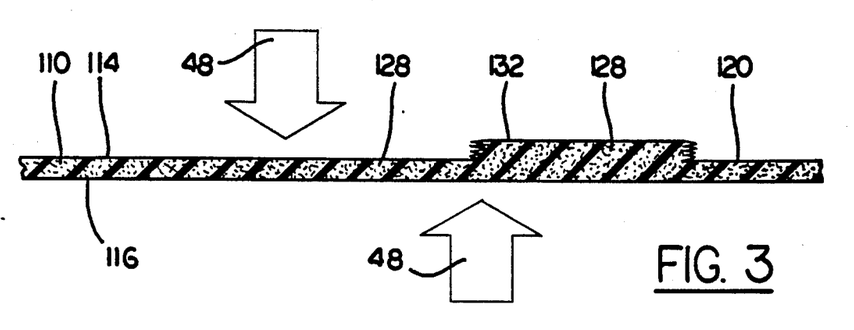
FIG. 3 is a cross section view of a portion of an intact septic barrier covering.

In FIG. 3, space 110 between flexible, water, air and microbe resistant layers 114 and 116 of covering 120 is at a reduced atmospheric pressure compared to environmental atmospheric pressure 48. Layers 114 and 116, under the pressure differential, squeeze open cell compressible foam 128 to yield a smaller space 110 and thinner covering. Seal and layer brake warning patch is compressed in like manner.

Figure 4:
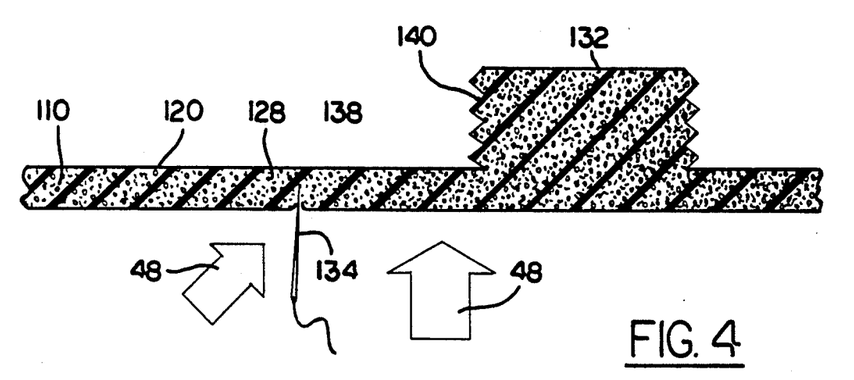
FIG. 4 is a cross section view of the portion shown in FIG. 3, punctured.

In FIG. 4, covering 120 is punctured by pin 134, which causes opening 138 in layer 116 through which environmental atmospheric pressure enters space 110. The resulting increase of atmospheric pressure in space 110 permits foam 128 to resile, increasing space 110, the thickness of covering 120, and the height of warning patch 132. Color in accordion ridges 140 increases visibility of the change in patch height.

Spacing between layers of a covering according to the present invention need not be limited to flexible means such as foam or flexible nodules. The spacing means, for example, can be a powder such as talc or other granular material supported between the layers by their confinement.

Figure 5:
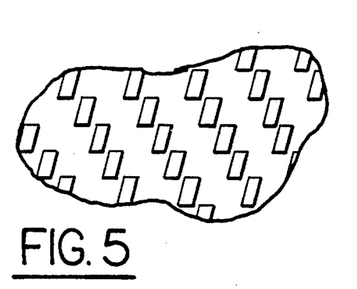
FIG. 5 is a perspective view of a spacer attached to a layer of a covering.
Figure 6:
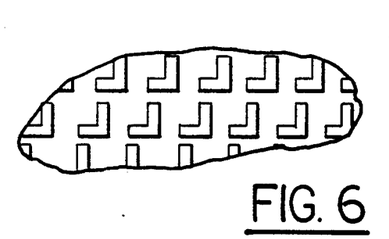
FIG. 6 is a perspective view of a spacer attached to a layer of a covering.
Figure 7:
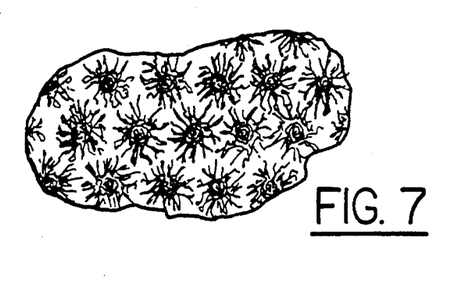
FIG. 7 is a perspective view of a spacer attached to a layer of a covering.

In FIG. 5, for another example a plurality of short, rigid, raised vertical ridges are used. Horizontal ridges would also be acceptable. Any shape will do, such as that of the rigid, or inflexible L shaped spacers shown in FIG. 6. In FIG. 7, flock is attached to a layer to space it from another layer.

Regardless of the shape or type of spacer, flexible or inflexible, it is preferred that the plurality of spacers between the layers permit passage of air within the space occupied by the spacers so that the various warning indicators can be responsive to a pressure change within the space.

Figure 8:
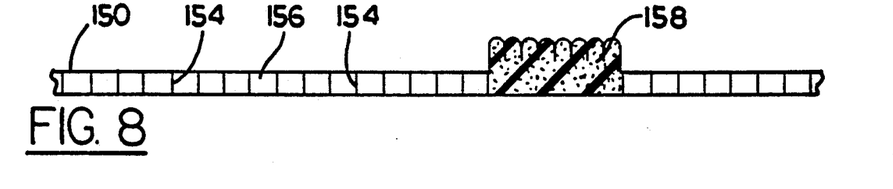
FIG. 8 is a cross section view of a portion of an intact septic barrier covering.

Septic barrier covering 150, shown in FIG. 8 includes rigid spacers 154 and compressible foam 158. Space 156 within covering 150 is at reduced atmospheric pressure, and foam 158 is therefore compressed. Spacers 154 are small and of a high population so that flexibility and tactile transfer through the covering, as in a surgical glove, is maintained.

Figure 9:
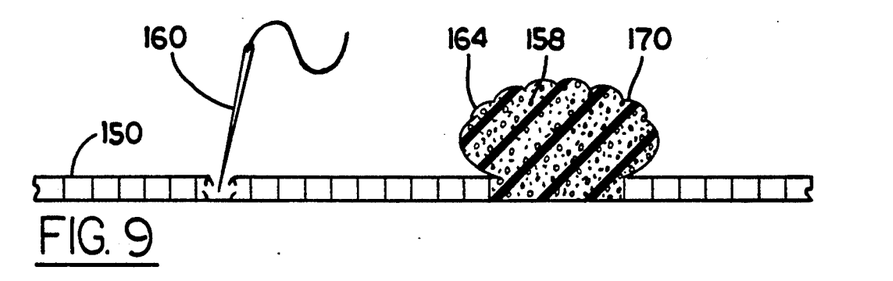
FIG. 9 is a cross section view of the portion shown in FIG. 8, punctured.

When as in FIG. 9, septic barrier covering 150 is penetrated by pin 160, atmospheric pressure within space 156 increases as explained earlier, and compressible foam 158 resiles to a larger volume, opening ridges 164 of patch 170 to reveal colored surfaces within the ridges. The expanded patch and colored surfaces warn of reduced effectiveness of the septic barrier provided by cover 150.

Figure 10:
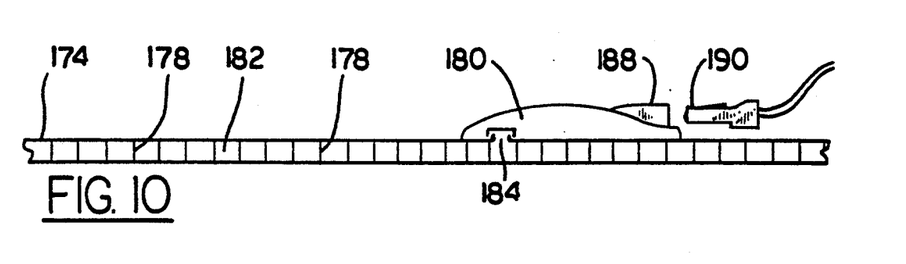
FIG. 10 is a cross section view of a portion of a septic barrier covering having switch warning means.

Referring to FIG. 10, covering 174 features rigid spacers 178, and electrical switch 180 that is responsive to pressure change, integrally attached to the cover, on the surface of the cover. Switch 180 is in atmospheric pressure communication with space 182 of covering 174 via opening 184. The switch includes female electrical connector 188 to receive male connector 190 with extension wire, for operation of a remote alarm.

The covering of the present invention can be used as a wrapper for a container of contaminated material, or for wrapping infectious material directly. It can be formed into a body covering such as a glove or condem for the user to protect the user from contact with infectious materials.

Figure 11:
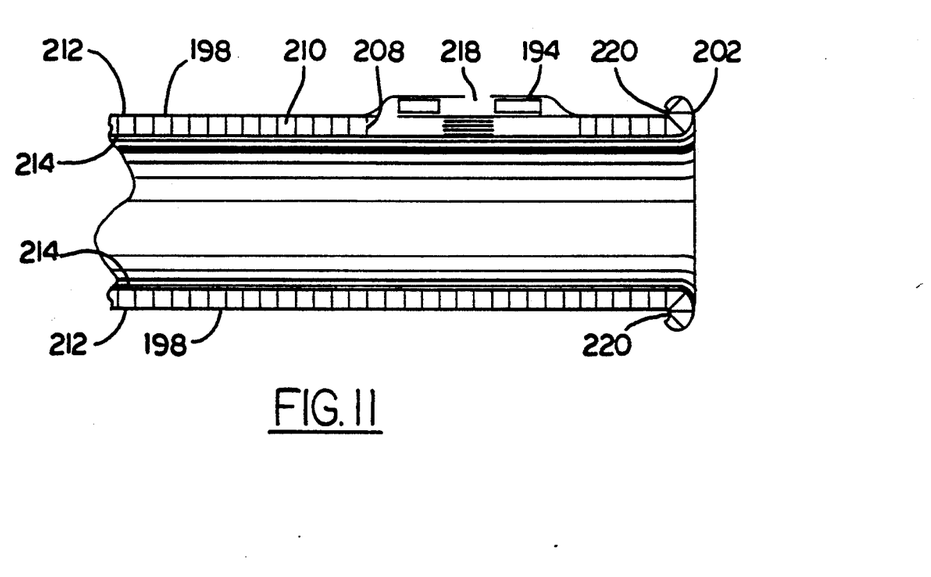
FIG. 11 is a cross section view of a rear portion of a condom according to the present invention.

In FIG. 11, audible alarm button 194 is integrally attached to covering 198 within covering 198, of condom 202. The alarm button is connected to the covering via opening 208 into space 210 for sensing the atmospheric pressure between layers 212 and 214 of covering 198. Opening 218 delivers audible chirps to the user if a break occurs in layer 212 or 214, or if the hermetic seal 220 between the two layers fails. To warn at the time that the condom is unwrapped, of a leak from a seal failure or manufacturing defect, an expanding patch is also included as described for FIG. 8.

Figure 12:
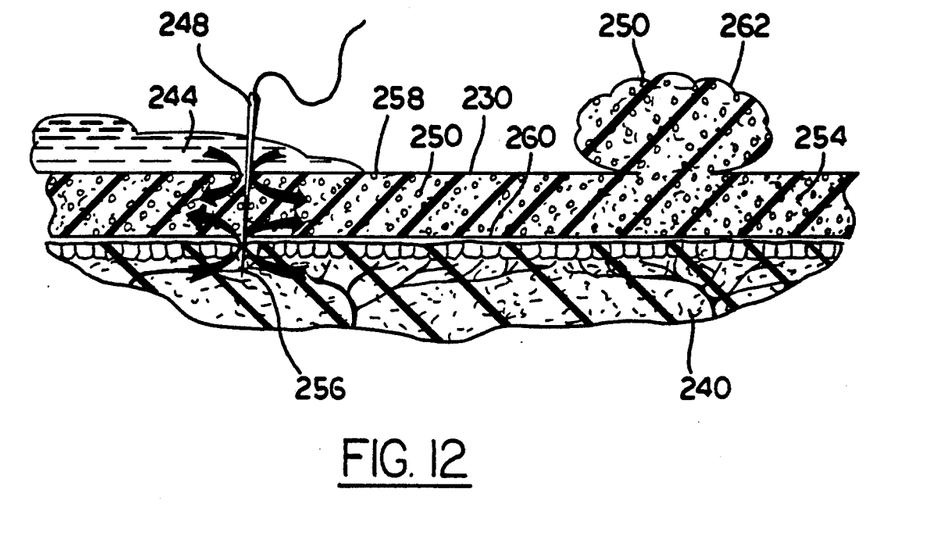
FIG. 12 is a cross section of a covering according to the invention, covering tissue and penetrated through to the tissue by a needle.

In addition to providing warning to the user of a break in one or more layers of the septic barrier covering, the covering provides protection against passing trough the septic barrier covering when the covering is punctured completely through. FIG. 12 shows this feature.

In FIG. 12, septic barrier covering 230 of a glove protects tissue from microbe contaminated liquid 244. When needle 248 penetrates through barrier covering 230 and into hand tissue 240, reduced atmospheric pressure in foam 250 filled space 254 between layers 258 and 260, draws liquid 244 that is entering through layer 258 into the foam before it can exit through the needle hole in layer 260 and contaminate needle wound 256 in the tissue. Simultaneously, blood from wound 256 is drawn into the foam via the needle hole in layer 260, washing some of the contamination from the needle surface from the wound into the foam. If the user of the glove did not feel or notice the puncture, expanding foam 254 raises patch 262, providing visual warning of the break in the barrier.

Thus it is seen that the present invention provides a septic barrier covering which provides audible, visual and tactile warning to the user of a break in a layer of the covering, and which directs contamination away from passage completely through the covering at a break through the covering.

Although the present invention has been described with respect to details of certain embodiments thereof, it is not intended that such details be limitations upon the scope of the invention. It will be obvious to those skilled in the art that various modifications and substitutions may be made without departing from the spirit and scope of the invention as set forth in the following claims.

I claim:
1. A septic barrier covering consisting of:
a first layer of flexible material, said first layer being resistant to passage of water, air and microbes through said first layer,
a second layer of flexible material, said second layer being resistant to passage of water, air and microbes through said second layer,
means for spacing, supported between said first and second layers for spacing said second layer from said first layer,
said first and second layers having space between them resulting from said means for spacing,
said first and second layers being hermetically sealed for maintaining reduced atmospheric pressure in said space between said first and second layers, and outside said space (70, 156) between said first and second layers, said covering including;

a hollow expandable patch (26, 132, 158, 262) on said first layer, compressible means (54, 158, 250) mounted in said hollow expandable patch for indicating an increase in reduced atmospheric pressure between said first and second layers, in passageway communication with said space between said first and second layers.

2. A septic barrier covering as described in claim 1, further comprising:

said compressible means for indicating comprising open cell foam.

3. A septic barrier covering as described in claim 1, further comprising:

hollow expandable patch which part when reduced atmospheric pressure between said first and second layers increases.

4. A septic barrier covering as described in claim 1, further comprising:

said folds on said hollow expandable patch including a colored surface which is bared directly to a viewer when said folds part.

5. A septic barrier covering as described in claim 1, further comprising:

said covering being formed in the shape of a surgical glove.

6. A septic barrier covering as described in claim 5, further comprising:

in said glove, resilient open cell foam means between said first and second layers, attached to a one of said first and second layers, for displacing a portion of one of said first and second layers in response to increase in reduced atmospheric pressure between said first and second layers.

7. A septic barrier covering comprising:

a first layer of flexible material, said first layer being resistant to passage of water, air and microbes through said first layer, a second layer of flexible material, said second layer being resistant to passage of water, air and microbes through said second layer, means for spacing, supported between said first and second layers for spacing said second layer from said first layer, and said first and second layers including spaced between them resulting from said means for spacing, said first and second layers being hermetically sealed for maintaining reduced atmospheric pressure in said space between said first and second layers, and means for indicating an increase in reduced atmospheric pressure between said first and second layers, in communication with said space between said first and second layers, said means for indicating comprising electrical switch means responsive to pressure change, connected to said barrier covering for sensing atmospheric pressure between said first and second layers.

8. A septic barrier covering as described in claim 7, further comprising:

means for generating an audible signal, connected to said electrical switch means for operation by said switch means.

9. A septic barrier covering as described in claim 8, further comprising:

said means for generating an audible signal being integrally attached to said barrier covering.

10. A septic barrier covering comprising:

a first layer of flexible material, said first layer being resistant to passage of water, air and microbes through said first layer, a second layer of flexible material, said second layer being resistant to passage of water, air and microbes through said second layer, means for spacing, supported between said first and second layers for spacing said second layer from said first layer, and said first and second layers including spaced between them resulting from said means for spacing, said first and second layers being hermetically sealed for maintaining reduced atmospheric pressure in said space between said first and second layers, and means for indicating an increase in reduced atmospheric pressure between said first and second layers, in communication with said space between said first and second layers, said means for spacing being compressible so that said means for spacing will compress to yield a smaller spacing when squeezed by said first and second layers, and said means for spacing further being resilient so that said means for spacing will resile when squeezing force from said first and second layers is reduced, said means for indicating comprising electrical switch means responsive to pressure change, connected to said barrier covering for sensing atmospheric pressure between said first and second layers.

11. A septic barrier covering as described in claim 10, further comprising:

means for generating an audible signal being integrally attached to said barrier covering, and connected to said electrical switch means for operation by said switch means.

12. A septic barrier covering as described in claim 11, further comprising:

said covering being formed in the shape of a condom.

13. A septic barrier covering as described in claim 12, further comprising:

means for generating an audible signal connected to said electrical switch means for operation by said switch means.

14. A septic barrier covering comprising:

a first layer of flexible material, said first layer being resistant to passage of water, air and microbes through said first layer, a second layer of flexible material, said second layer being resistant to passage of water, air and microbes through said second layer, means for spacing, supported between said first and second layers for spacing said second layer from said first layer, and said first and second layers including spaced between them resulting from said means for spacing, said first and second layers being hermetically sealed for maintaining reduced atmospheric pressure in said space between said first and second layers, and means for indicating an increase in reduced atmospheric pressure between said first and second layers, in communication with said space between said first and second layers, said covering being formed in the shape of a surgical glove, in said glove, said means for indicating comprising electrical switch means responsive to pressure change, connected to said barrier covering for sensing atmospheric pressure between said first and second layers.

15. A septic barrier covering as described in claim 14, further comprising:

in said glove, means for generating an audible signal being integrally attached to said barrier covering, and connected to said electrical switch means for operation by said switch means.

16. A septic barrier covering consisting of:

a first layer of flexible material, said first layer being resistant to passage of water, air and microbes through said first layer, a second layer of flexible material, said second layer being resistant to passage of water, air and microbes through said second layer, means for spacing, supported between said first and second layers for spacing said second layer from said first layer, said first and second layers including spaced between them resulting from said means for spacing, said first and second layers being hermetically sealed for maintaining reduced atmospheric pressure in said space between said first and second layers, said space between said first and second layers being at reduced atmospheric pressure, and means on said first layer for indicating an increase in said atmospheric pressure between said first and second layers, in communication with said space between said first and second layers.

* * * * *

UNITED STATES PATENT AND TRADEMARK OFFICE
CERTIFICATE OF CORRECTION

PATENT NO. : 5,317,760
DATED : June 7, 1994
INVENTOR(S) : Paul S. Best

It is certified that error appears in the above-identified patent and that said Letters Patent is hereby corrected as shown below:

Col. 7, line 15,

In Claim 3, after "further comprising:", before "hollow expandable patch", insert --folds on said--

Col. 7, line 18,

In Claim 4, after "as described in claim", delete "1", and replace therewith --3--

Signed and Sealed this

Sixth Day of September, 1994

Attest:

BRUCE LEHMAN

Attesting Officer     Commissioner of Patents and Trademarks